United States Patent [19]

Tobar

[11] Patent Number: 5,245,409
[45] Date of Patent: Sep. 14, 1993

[54] TUBE SEAM WELD INSPECTION DEVICE
[75] Inventor: Ronald A. Tobar, Franklin, Ind.
[73] Assignee: Arvin Industries, Inc., Columbus, Ind.
[21] Appl. No.: 800,853
[22] Filed: Nov. 27, 1991
[51] Int. Cl.⁵ .................................................. G01B 11/24
[52] U.S. Cl. .................................... 356/375; 356/376; 358/101; 358/106
[58] Field of Search ............... 356/373, 375, 376, 237; 358/101, 106

[56] References Cited

U.S. PATENT DOCUMENTS

| | | |
|---|---|---|
| 3,812,376 | 5/1974 | Takeyama et al. . |
| 3,816,649 | 6/1974 | Butters et al. . |
| 3,976,382 | 8/1976 | Westby ................... 356/376 |
| 4,001,497 | 1/1977 | Bosworth ................ 358/101 |
| 4,111,557 | 9/1978 | Rottenkolber et al. . |
| 4,188,544 | 2/1980 | Chasson ................. 356/376 |
| 4,410,787 | 10/1983 | Kremers et al. ....... 358/107 |
| 4,492,847 | 1/1985 | Masaki et al. . |
| 4,493,968 | 1/1985 | Brown . |
| 4,498,776 | 2/1985 | Smith ..................... 356/375 |
| 4,498,778 | 2/1985 | White . |
| 4,541,721 | 9/1985 | Dewar .................... 356/376 |
| 4,542,279 | 9/1985 | Case, Jr. et al. . |
| 4,567,347 | 1/1986 | Ito et al. . |
| 4,568,816 | 2/1986 | Casler, Jr. . |
| 4,575,304 | 3/1986 | Nakagawa et al. . |
| 4,590,356 | 5/1986 | Povlick et al. . |
| 4,596,919 | 6/1986 | Kremers et al. . |
| 4,616,121 | 10/1986 | Clocksin et al. . |
| 4,650,333 | 3/1987 | Crabb et al. ........... 356/376 |
| 4,666,303 | 5/1987 | Pryor ..................... 356/375 |
| 4,667,082 | 5/1987 | Shibata et al. . |
| 4,683,493 | 7/1987 | Taft et al. .............. 358/101 |
| 4,696,047 | 9/1987 | Christian et al. ...... 382/8 |
| 4,724,301 | 2/1988 | Shibata et al. . |
| 4,734,766 | 3/1988 | Shiozumi et al. . |
| 4,741,621 | 5/1988 | Taft et al. .............. 356/376 |
| 4,791,482 | 12/1988 | Barry et al. . |
| 4,801,207 | 1/1989 | Williams ............... 356/376 |
| 4,811,410 | 3/1989 | Amir et al. ............. 382/8 |
| 4,812,614 | 3/1989 | Wang et al. . |
| 4,839,994 | 6/1989 | Heesemann . |
| 4,907,169 | 3/1990 | Lovoi ...................... 358/101 |
| 4,917,498 | 4/1990 | Geary ..................... 356/357 |
| 4,965,665 | 10/1990 | Amir . |
| 4,979,815 | 12/1990 | Tsikos . |
| 4,988,202 | 1/1991 | Nayar et al. . |

FOREIGN PATENT DOCUMENTS

| | | | |
|---|---|---|---|
| 230006 | 10/1986 | Japan .................... 356/237 |
| 269007 | 11/1986 | Japan .................... 356/376 |
| 132908 | 5/1989 | Japan .................... 356/237 |
| 209307 | 8/1989 | Japan .................... 356/376 |

OTHER PUBLICATIONS

Saburo Ishiro et al., "Construction and Operation of Ultra Heavy Wall and Small Diameter HF-ERW Pipe Mill", NKK Technical Review, No. 53, pp. 28–35, 1988.
Fryer New Product Bulletin, 1989, entitled *Light Sectioning*.
Oldelft, *The Robot's Eye*, undated.
Jos. A. C. Appels, *Applications of Seampilot Optical Profile Sensors for Arc Welding* undated.
MVS, *Laservision Seam Tracking/Adaptive Welding System Three Axis Welding Machine Control* Apr. 1990.
Article, *Laser Tracker Leads Welding* undated.
The Fabricator, *How a Flat Strip Becomes a Welded Tube*, reprint from Oct. 1987.

*Primary Examiner*—F. L. Evans
*Attorney, Agent, or Firm*—Barnes & Thornburg

[57] ABSTRACT

The invention provides a method and apparatus for on-line, real-time imaging and inspecting a seam weld on a moving tube in a conventional tube forming environment. The apparatus is in a compact container sealed from workplace contaminants. A planar light source directs a steady plane of light by using mirrors, through an aperture in the container and onto the tube seam at a 45° angle relative to the tube axis, forming a light pattern on the moving tube. A camera in the container images the light, again at 45° relative to the tube axis, and said image is displayed remotely on a conventional video monitor. An operator interprets the light pattern image and adjusts the tube forming apparatus accordingly.

37 Claims, 3 Drawing Sheets

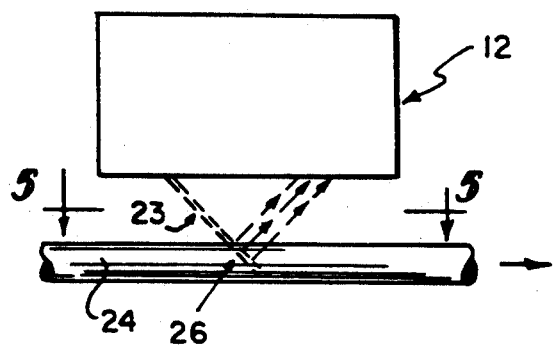
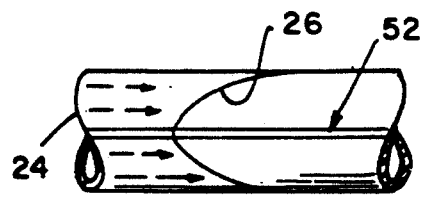
FIG. 4
FIG. 5
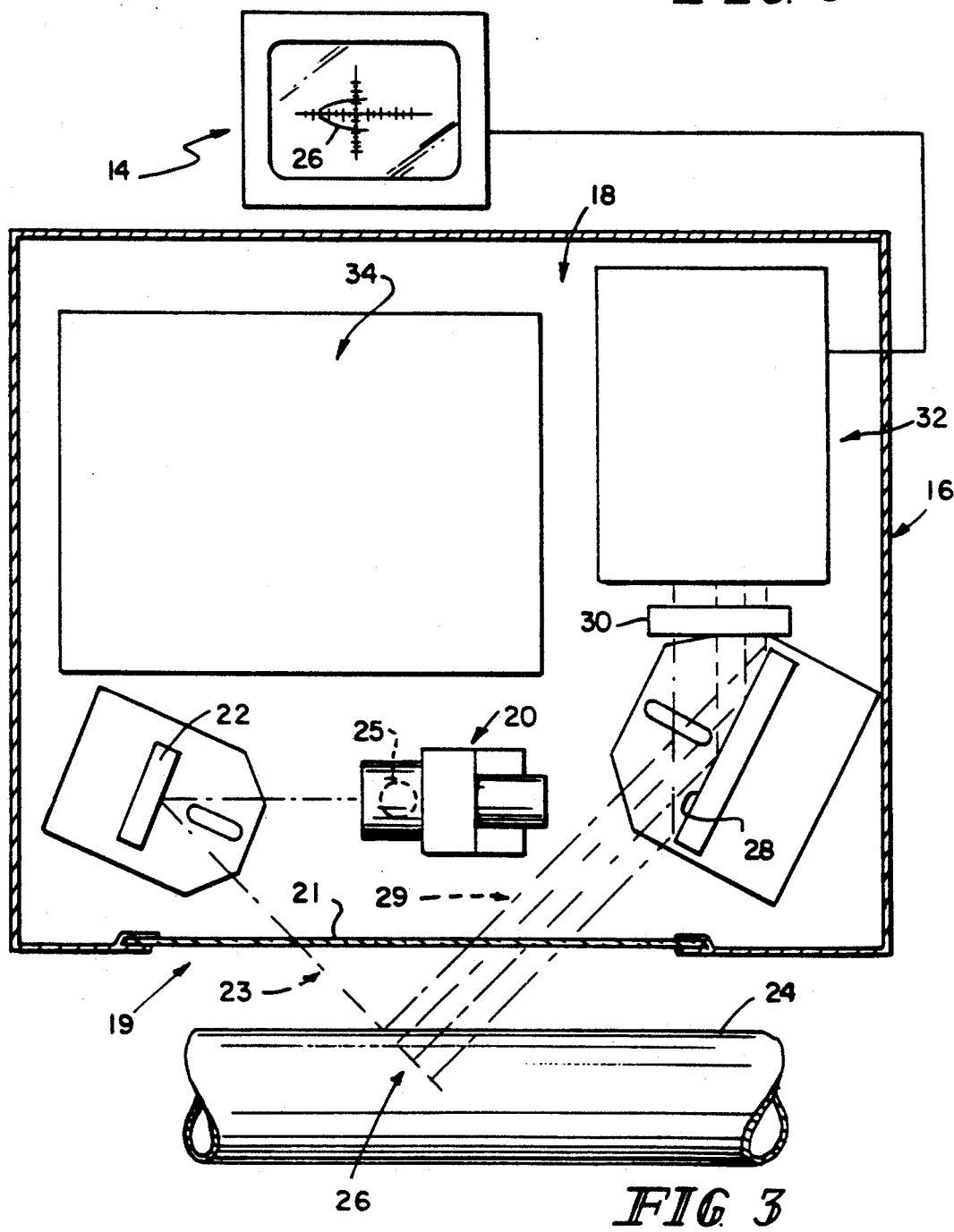
FIG. 3

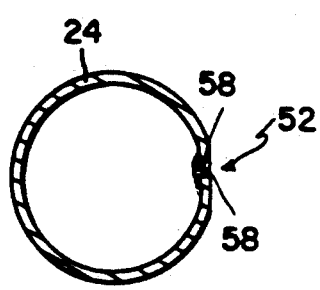
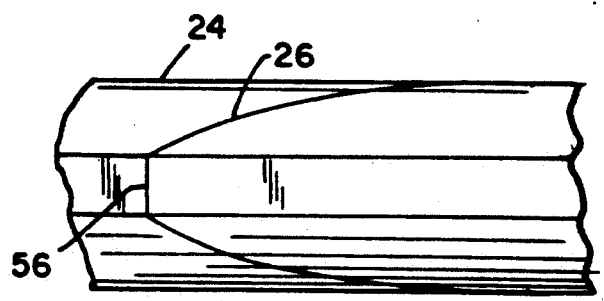
FIG. 6a  FIG. 6b
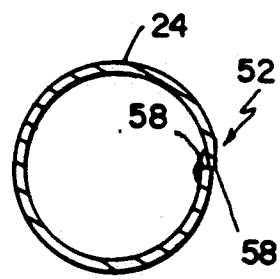
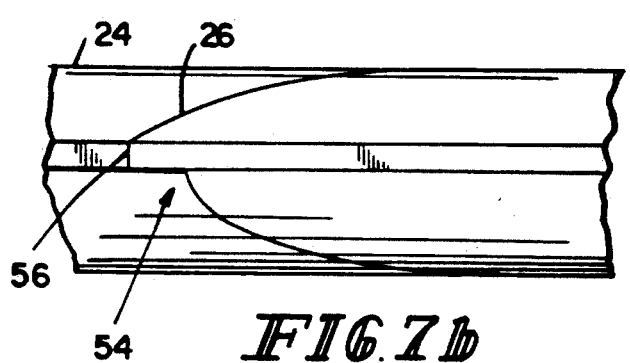
FIG. 7a  FIG. 7b
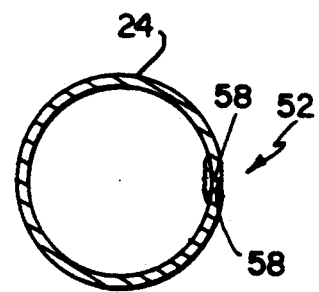
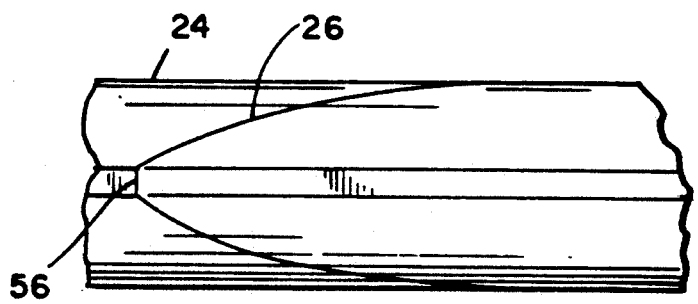
FIG. 8a  FIG. 8b

TUBE SEAM WELD INSPECTION DEVICE

BACKGROUND AND SUMMARY OF THE INVENTION

This invention relates to imaging and inspection devices and particularly to tubing weld seam inspection devices used in combination with conventional tube forming machines.

A tube forming machine is a device which takes strip stock from a roll and, through a series of operations, converts it into a welded tube. The first step of the process is edge conditioning where rust and uneven edges are removed. The strip then passes between a series of rollers mounted on shafts where a curve is formed in the strip. At every pass after that, the radii gets smaller so that the strip takes the form of a cylinder in preparation for welding.

In a typical manufacturing operation, the tubing thus formed is moving along its longitudinal axis at a high rate of speed and, therefore, timely inspection is critical. Without such timely inspection, tremendous amounts of material would be wasted due to the improper seam alignment and the resulting low quality seam weld.

Ideally when tubing is formed from strip stock on conventional tube forming machines, both edges of the strip are joined in the weld box at the same height. Previous to the present invention, the most common method for inspection for edge alignment was for the operator to hold his gloved hand on the weld seam. This was not a desirable condition for safety and accuracy reasons. Off-line, the inspector could cut samples and inspect them under a microscope, but that required too much time to detect and take corrective action. What was needed was an on-line, non-contact, real-time monitoring system to measure edge alignment. However, as a result of the edge conditioning, tube forming, and welding processes, the environment becomes very dirty, and it is in this dirty environment that the inspection is expected to take place.

The present invention provides a low cost, simple and easy to implement vision system to detect edge misalignment, and is designed to operate in a dirty environment. In accordance with the present invention, a live image is displayed on a monitor.

Imaging and inspection systems are known in the prior art. See, for example, Shiozumi et al., U.S. Pat. No. 4,734,766; Tsikos, U.S. Pat. No. 4,979,815; Heesemann, U.S. Pat. No. 4,839,994; Rottenkolber et al., U.S. Pat. No. 4,111,557; White, U.S. Pat. No. 4,498,778; Wang et al., U.S. Pat. No. 4,812,614; Clocksin et al., U.S. Pat. No. 4,616,121; Masaki et al., U.S. Pat. No. 4,492,847; Nayar et al., U.S. Pat. No. 4,988,202; Kremers et al., U.S. Pat. No. 4,596,919; Case, Jr. et al., U.S. Pat. No. 4,542,279; Povlick et al., U.S. Pat. No. 4,590,356; Fryer New Product Bulletin, 1989, Subject: Light Sectioning; and Oldelft, The Robot's Eye, undated.

The present invention constitutes a significant improvement over the prior art because it is relatively low cost, easy to install, and effective for the purpose intended, i.e., readily to show that the seam weld produced by a conventional tube forming machine is out of specification. For instance, the prior art shows lasers used to monitor seams in manufacturing processes, but the prior art systems involve complicated laser scanning techniques and monitoring techniques for laser scanning, or complicated algorithms to analyze the data provided by the laser image.

According to the present invention an apparatus is provided for visualizing a longitudinal seam weld on a moving tube in a conventional tube forming environment, wherein the apparatus comprises means for projecting a steady plane of light on the tube seam weld as the tube moves longitudinally past the projecting means, means for imaging a reflection of the projected light from the tube seam weld, and means for displaying the reflection image. It also provides an apparatus for visualizing a seam weld on a moving tube, wherein the apparatus comprises a laser light source, lens means for forming the laser light into a steady plane of light, a plurality of mirrors to direct the plane of light to intersect the tube seam weld and to direct the reflection of the intersection to a camera, and a monitor to display the reflection imaged by the camera.

The present invention also provides an apparatus for visualizing a seam weld on a tube moving longitudinally in the direction of its axis, wherein the apparatus comprises a container formed to include an interior region and an aperture facing the moving tube and its seam weld, the container being positioned in spaced-apart relation to the tube seam weld. It further comprises light means for providing a planar light, the light means being mounted in the interior region, means for directing the planar light out of the interior region of the container through the aperture to intersect the tube seam weld, wherein the directing means are mounted in the interior region. It further comprises means for imaging the light pattern on the tube seam weld, the imaging means being mounted in the interior region, means for displaying the imaged points of intersection connected to the imaging means, the displaying means being positioned outside the container, source means for supplying electrical power to the light source and the imaging means, the power source means being mounted in the interior region, and transparent means for covering the aperture to keep workplace contaminants out of the interior region.

The present invention also provides an apparatus for optically determining departures in shape of a workpiece, where the apparatus comprises a container formed to include an interior region and an aperture, the container being positioned in spaced-apart relation to the workpiece, a planar light source mounted in the interior region, and a camera mounted in the interior region. It further comprises a plurality of mirrors arranged in the interior region to direct the planar light through the aperture to intersect the workpiece and to direct the reflection of the light pattern which passes through the aperture toward the camera, a power supply mounted in the interior region to provide electrical power to the apparatus, and a transparent aperture cover attached to the container in an aperture closing position to keep workplace contaminants out of the interior region.

The present invention further provides an edge alignment measuring system for inspecting alignment of a pair of edges of a strip that abut one another at a seam weld to form a tube, wherein the system comprises means for projecting a steady plane of coherent light across the seam of the tube to produce a first light pattern on one of the edges and a second light pattern on the other edge. It further provides means for displaying the first and second light patterns side-by-side to indicate a discontinuity between the first and second light patterns so that misalignment of the edges relative to one another is detected.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 3 is a sectional view of an alternative embodiment of the imaging system showing the layout of components;

FIG. 4 generally shows a spaced-apart relationship between the weld seam inspection device and the tube;

FIG. 5 is a view looking down on the tube from the inspection device along the line 5—5 of FIG. 4 showing the light pattern on the tube;

FIGS. 6, 7, and 8 show variations of the light pattern based on degree of match and amount of scarf;

FIG. 6a is a cross section of a tube having a good match with a deep scarf;

FIG. 6b shows the light pattern associated with the match and scarf conditions of FIG. 6a;

FIG. 7a is a cross section of a tube having a poor match with a shallow scarf;

FIG. 7b shows the light pattern associated with the match and scarf conditions of FIG. 7a;

FIG. 8a shows a good match with a good scarf; and

FIG. 8b shows a light pattern associated with the match and scarf conditions of FIG. 8a.

DETAILED DESCRIPTION OF THE DRAWINGS

Figure 1:
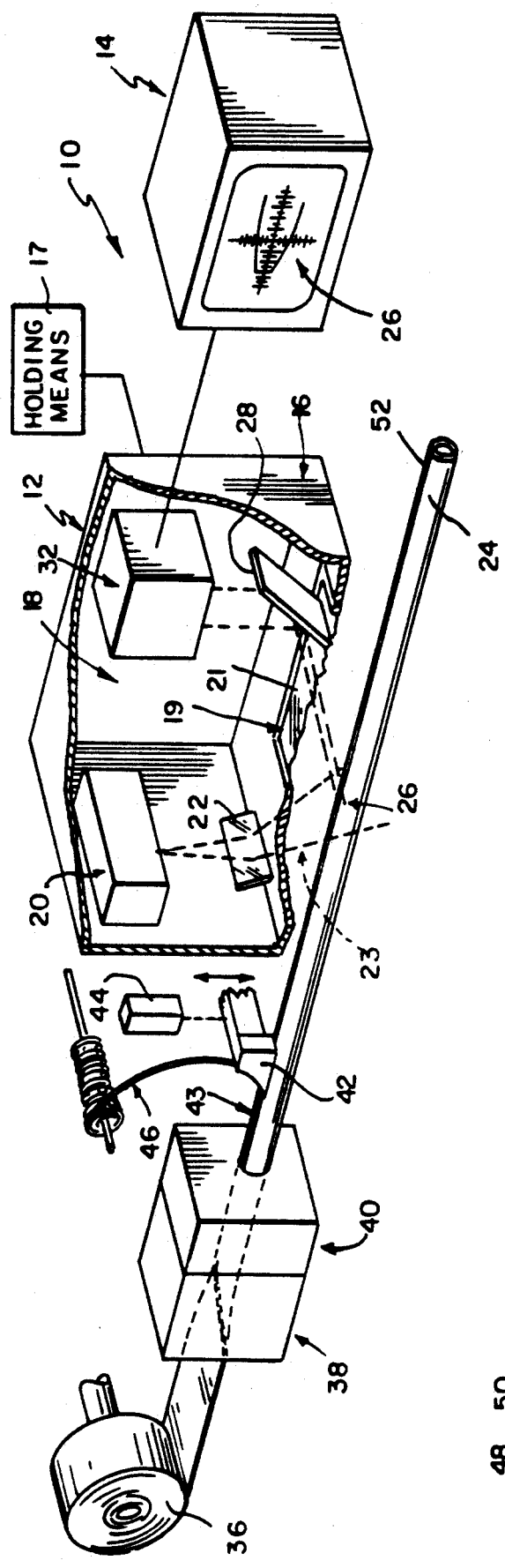
FIG. 1 shows an illustrative embodiment of the weld seam inspection device, partially broken away, in position on a tube forming and welding production line.
Figure 2:
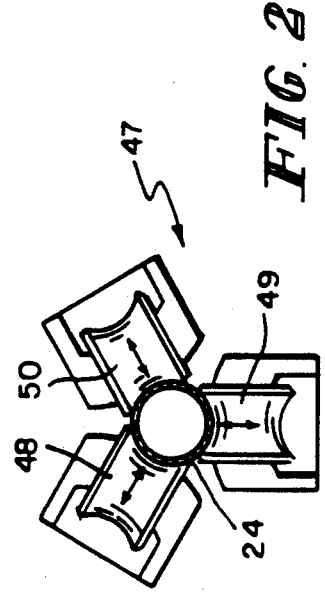
FIG. 2 is a representation of three rollers in a weld box used to control the match of a seam tube.

An illustrative embodiment (FIG. 1) of a weld seam inspection device 10 for tube welding comprises an imaging system 12 and a monitor 14 to display an image. The imaging system 12 comprises a container 16 formed to include an interior region 18 and an aperture 19. Holding means 17 is provided to hold the container 16 in a fixed position above a moving tube 24 as shown in FIG. 1. A transparent aperture cover 21 is attached to the container to keep contaminants out of the container. A planar light source 20, such as the LaserMax, Inc. Model MDL-200-670-5 or a Melles Griot Model S1167/P Line Projector, is attached to the interior region 18. The plane of light begins as a spot and cylindrical lens 25 spreads the light at a 30° angle so that it is about 3 inches wide at 6 inches from the source. A mirror 22, also attached to the interior region 18, reflects the planar light from the source 20 through the aperture 19 to intersect a tube 24 forming a light pattern 26. A second mirror 28 attached to the interior region 18 directs an image of the light pattern 26 passing through the aperture 19 into a camera 32, such as the Video Runner Model 1020 manufactured by Marshall Electronics, Inc. of Culver City, Calif., which is attached to the interior region 18. A conventional video monitor 14 is electrically connected to the camera 32 and displays the image of the light pattern 26 received by the camera 32. Thus, the container 16 holds the light source 20, mirrors 22 and 28, and camera 32. Therefore, as shown in FIG. 3, container 16 acts as a means for holding the light projecting and reflection imaging means in a fixed position relative to the longitudinally moving tube 24. In an alternative embodiment, as shown in FIG. 3, a power supply 34 is also mounted in the interior region 18 and provides electrical power to components of the imaging system 12. It will be appreciated that the power supply need not be so mounted, but rather power could be supplied by means connected to an external source.

FIG. 1 illustrates the principles involved in the present invention, and it will be appreciated that the light source 20, mirror 22, aperture 19, mirror 28 and camera 32 may be located and positioned at various angles and distances in accordance with the present invention. It has been found that the 45° projection and 45° reflection is ideal and preferable for the tube forming machine environment in which the present invention works. In particular, the present invention is used in combination with conventional tube forming and welding machines and is preferably made such that it will fit in the very tight and irregularly shaped area just above the tube after it is welded and scarfed.

In operation, strip material 36 is fed into a tube shaping apparatus 38 and then into a welding apparatus 40. It will be appreciated that the shaping apparatus 38 and welder 40 ar ⓡillustrated diagrammatically in FIG. 1, and that these apparatus are very well-known and need not be discussed in detail. There are several tube forming machine suppliers from which such machines can be acquired. Typical suppliers are Yoder Manufacturing Co., Bedford Heights, Ohio and T&H Machine Co., Addison, Ill. Upon exiting the welding apparatus 40 the tube 24 passes under a scarfing tool 42 which is moved up and down by an adjustment mechanism 44 to remove the desired amount of scarf 46 from the weld 43. After scarfing, the tube 24 passes under the imaging system 12 where a steady plane of light 23 is directed onto the tube 24 forming a light pattern 26. The light pattern 26 is imaged by the camera 32, and the image is displayed on a monitor 14.

In the alternative embodiment of FIG. 3, the planar light source 20 directs a plane of light 23 to the first mirror 22 which reflects the plane of light 23 through the aperture 19 and onto the tube 24 illustratively and preferably at an angle of incidence of 45° to the vertical. The reflection of the light pattern 26 reflected from the tube 24 illustratively and preferably at an angle of 45° to the vertical is received by the mirror 28 through the aperture 19 and directed to the lens 30 and camera 32. It will be appreciated that the light source 20 and camera 32 could be positioned to obviate the need for mirrors 22 and 28. However, the embodiment of FIG. 3 represents a compact arrangement suitable to the typical tube forming machine workplace environment. The monitor 14 displays the image viewed by the camera 32, where it is interpreted by an operator to determine the degree of match and the degree of scarf. When the degree of scarf is determined to be outside of acceptable limits, the operator can adjust the scarfing tool 42. When the edges of the seam 52 do not match properly, the operator can adjust the weld box 47 located within the welding apparatus 40 by adjusting the rollers 48, 49 and 50 inwardly or outwardly as necessary. It will be appreciated that such tube forming machine rollers 48, 49 and 50 are conventional.

FIG. 6b shows the light pattern 26 on the tube 24 when the tube seam edges 58 match properly, but where the scarfing tool 42 cut too deep, as indicated by the relatively long straight portion 56 of the light pattern 26. FIG. 6a shows the cross section of a tube with the match and scarf conditions that match the light pattern of FIG. 6b.

FIG. 7b shows the light pattern 26 on the tube 24 when the tube seam edges 58 do not match properly, producing a discontinuity 54 in the light pattern 26. The relative shortness of the straight portion of 56 the light pattern 26 indicates a shallow scarf. FIG. 7a shows the cross section of a tube with the match and scarf conditions that match the light pattern of FIG. 7b.

FIG. 8b shows the light pattern 26 on the tube 24 when the tube seam edges 58 match properly and the relative shortness of the straight portion 56 of the light pattern 26 indicates a good scarf. FIG. 8a shows the cross section of a tube with the match and scarf conditions that match the light pattern of FIG. 8b.

Although the invention has been described in detail with reference to certain preferred embodiments, variations and modifications exist within the scope and spirit of the invention as described and defined in the following claims.

What is claimed is:

1. An apparatus for visualizing a longitudinal seam weld on a moving tube in combination with a tube forming machine which forms tube from a strip of flat metal stock, the strip having edges capable of being misaligned when the strip is formed into a tube, the apparatus comprising
    means for detecting a misalignment of the edges, the means for detecting including means for projecting a steady plane of light on the tube seam weld as the tube moves longitudinally past said projecting means and means for imaging a reflection of the projected light from the tube seam weld, and
    means for displaying the reflection image.

2. The apparatus of claim 1, wherein the projecting means includes a laser light source, lens means through which the laser light is projected, and mirror means for directing the plane of light to intersect the tube seam weld and to direct the reflection of the intersection to the imaging means.

3. The apparatus of claim 2, further comprising means for holding the projecting and imaging means in a fixed position above the longitudinally moving tube.

4. The apparatus of claim 1, wherein the projecting means and the imaging means are in a fixed position relative to the longitudinally moving tube above the seam weld.

5. The apparatus of claim 1, wherein the imaging means includes a camera and a mirror directing the reflection of the projected light from the tube seams weld to the camera.

6. The apparatus of claim 5, further comprising a container housing the projecting means, mirror, and camera.

7. The apparatus of claim 6, wherein the container is formed to include a window opening toward the tube seam weld on the moving tube, the projecting means is located to project the steady plane of light through the window to reach the tube seam weld on the moving tube, and the window is sized to allow the reflection of the projected light to pass from the tube seam weld to the camera through the window.

8. The apparatus of claim 7, further comprising a transparent cover attached to the container and fitted in the window to prevent workplace contaminants from passing through the window to reach the projecting means and the imaging means in the container.

9. The apparatus of claim 4, wherein the imaging means includes a camera and a mirror directing the reflection of the projected light from the tube seam weld to the camera.

10. An apparatus for visualizing a seam weld on a moving tube in combination with a tube forming machine which forms tube from a strip of flat metal stock, the apparatus comprising
    a laser light source,
    lens means for forming a laser light into a steady plane of light,
    mirror means for directing the plane of light to intersect the tube seam weld and to direct the reflection of the intersection to a camera, and
    monitor means to display the reflection imaged by the camera.

11. The apparatus of claim 10, further comprising a power supply and a container formed to define an interior region configured to hold the light source, lens means, mirrors, and power supply.

12. The apparatus of claim 11, further comprising means for holding the container in a fixed position above the moving tube.

13. The apparatus of claim 10, further comprising a container housing the laser light source, mirror means, and lens means.

14. The apparatus of claim 13, wherein the container is formed to include a window opening toward the tube seam weld on the moving tube, the laser light source and mirror means are located to project the steady plane of light through the window to reach the tube seam weld on the moving tube, and the window is sized to allow the reflection of the projected light to pass from the tube seam weld to the camera through the window.

15. An apparatus for visualizing a seam weld on a tube moving longitudinally in the direction of its axis, the apparatus comprising
    a container formed to include an interior region and an aperture facing the moving tube and its seam weld, the container being positioned in spaced-apart relation to the tube seam weld,
    light means for providing a steady planar light, the light means being mounted in the interior region,
    means for directing the planar light out of the interior region of the container through the aperture to intersect the tube seam weld to form a light pattern on the tube, the directing means being mounted in the interior region,
    means for imaging the light pattern on the tube seam weld, the imaging means being mounted in the interior region,
    means for displaying the imaged light pattern connected to the imaging means, the displaying means being positioned outside the container,
    source means for supplying electrical power to the light source and the imaging means, the power source means being mounted in the interior region, and
    transparent means for covering the aperture to keep workplace contaminants out of the interior region.

16. The apparatus of claim 15, wherein the providing means comprises a laser light and cylindrical lens, and the directing means comprises a plurality of mirrors positioned to direct the steady planar light through the aperture and onto the tube seam weld and to direct the reflection of the points of intersection of the planar light and the tube seam weld into the imaging means.

17. An apparatus for optically determining departures in shape of a workpiece in combination with a manufacturing environment, the apparatus comprising a container formed to include an interior region protected from the environment and an aperture, the container being positioned in spaced-apart relation to the workpiece, a planar light source mounted in the interior region, a camera mounted in the interior region, a plurality of mirrors arranged in the interior region to direct the planar light through the aperture to intersect the workpiece to form a light pattern on the workpiece and to direct the reflection of the light pattern which passes through the aperture toward the camera, a power supply mounted in the interior region to provide electrical power to the apparatus, a transparent aperture cover attached to the container in an aperture-closing position to keep workplace contaminants out of the interior region.

18. An edge alignment measuring system for inspecting alignment of a pair of edges of a strip that abut one another at a seam weld to form a tube in a tube forming machine, the system comprising means for projecting a steady plane of coherent light across the seam of the tube after it is welded to produce a first light pattern on a first of the edges and a second light pattern on a second of the edges, and means for displaying the first and second light patterns side-by-side to indicate discontinuity between the first and second light patterns so that misalignment of the first and second edges relative to one another is detected.

19. The system of claim 18, wherein the projecting means includes means for aiming the light source at the tube at about an angle of 45° relative to the weld seam to produce the first and second light patterns.

20. The system of claim 18, wherein the projecting means includes a laser light source, a cylindrical lens and at least one mirror, and the displaying means includes at least one mirror, a camera, and a viewing screen.

21. The system of claim 20, further comprising a container formed to include an aperture and an interior region configured to hold the light source, the mirrors, and the camera.

22. The system of claim 21, further comprising a transparent means for covering the aperture to allow the laser light to pass out of the interior region through the aperture while keeping workplace contaminants out of the interior region.

23. An edge alignment measuring system for inspecting a pair of edges of a strip that abut one another at a seam weld to form a tube, the system comprising a container formed to include an interior region and an aperture, means for projecting a steady plane of coherent light across the seam of the tube to produce a first light pattern on a first of the edges and a second light pattern on a second of the edges, where the projecting means is mounted inside the container, means for displaying the first and second light patterns side-by-side to indicate discontinuity between the first and second light patterns so that a misalignment of the first and second edges relative to one another is detected, and a transparent aperture cover mounted on the container.

24. The system of claim 23, wherein the projecting means includes a laser light source, a cylindrical lens, and at least one mirror, and the displaying means includes at least one mirror, a camera, and a viewing screen.

25. The system of claim 24, wherein the displaying means mirror and camera are mounted inside the container.

26. The system of claim 25, further comprising means for aiming the light source through the aperture at the tube at an angle of about 45° relative to the weld seam to produce the first and second light patterns.

27. A method for inspecting the alignment of a pair of edges of a strip that abut one another at a weld seam to form a tube, the method comprising the steps of projecting a first light pattern on a first of the edges and a second light pattern on a second of the edges, displaying the first and second light patterns side-by-side to indicate one of a match and a discontinuity to detect a misalignment of the first and second edges relative to one another.

28. The method of claim 21, wherein the projecting step includes the step of aiming a light source at the tube at an angle of about 45° relative to the weld seam to produce the first and second patterns.

29. The method of claim 28, further comprising the step of moving the tube longitudinally under the light patterns.

30. The method of claim 27, wherein the displaying step further includes the steps of receiving a reflected image of the first and second light patterns on a mirror and using a camera to transmit the reflected image from the mirror to a viewing screen.

31. A method for inspecting the alignment of a pair of edges of a strip that abut one another at a weld seam to form a tube, the method comprising the steps of projecting a first light pattern on a first of the edges and a second light pattern on a second of the edges, moving the tube longitudinally under the light patterns, and displaying the first and second light patterns side-by-side to indicate discontinuity to detect a misalignment of the first and second edges relative to one another.

32. The method of claim 31, wherein the projecting step includes the step of aiming a light source at the tube at an angle of about 45° relative to the weld seam to produce the first and second light patterns.

33. The method of claim 31, wherein the displaying step further includes the steps of receiving a reflected image of the first and second light patterns on a mirror while the tube moves and using a camera to transmit the reflected image from the mirror to a viewing screen.

34. A measuring system for inspecting a cut made by a weld bead scarfing tool on a tube moving longitudinally in the direction of its axis at a tube seam extending along the axis and receiving a weld bead, the measuring system comprising means for projecting a steady plane of coherent light across the cut made by the weld bead scarfing tool to produce a first light pattern on a first side of the tube seam and a second light pattern on a second side of the tube seam, and means for displaying the first and second light patterns side-by-side to indicate discontinuity between the first and second light patterns so that the depth of the cut made by the weld beam scarfing tool is detected.

35. The system of claim 34, wherein the displaying means includes a camera and a mirror directing a reflection of the first and second light patterns to the camera.

36. The system of claim 35, further comprising a container housing the projecting means, mirror, and camera.

37. The apparatus of claim 36, wherein the container is formed to include a window opening toward the cut made by the weld bead scarfing tool, the projecting means is located to project the steady plane of coherent light through the window to reach said cut, and the window is sized to allow reflection of the first and second light patterns to pass to the camera through the window.

* * * * *